(12) United States Patent
Debur et al.

(10) Patent No.: US 10,881,852 B2
(45) Date of Patent: Jan. 5, 2021

(54) DEVICE, SYSTEM AND APPARATUS FOR FUNCTIONAL ELECTRICAL STIMULATION OF MUSCLE

(71) Applicant: Gokula Education Foundation (Medical), Bangalore (IN)

(72) Inventors: Ramesh Debur, Bangalore (IN); Viswanath Talasila, Bangalore (IN); Vinay Sridhar, Bangalore (IN); Raghavendra Padmanabh, Bangalore (IN); Pramod Jayaram, Bangalore (IN); Aditi Bhandarkar, Bangalore (IN)

(*) Notice: Subject to any disclaimer, the term of this patent is extended or adjusted under 35 U.S.C. 154(b) by 0 days.

(21) Appl. No.: 15/424,807

(22) Filed: Feb. 4, 2017

(65) Prior Publication Data

US 2017/0224985 A1 Aug. 10, 2017

(51) Int. Cl.
*A61N 1/36* (2006.01)
*A61B 5/0488* (2006.01)
*A61N 1/04* (2006.01)

(52) U.S. Cl.
CPC ........ *A61N 1/36003* (2013.01); *A61B 5/0488* (2013.01); *A61N 1/0452* (2013.01); *A61N 1/36014* (2013.01)

(58) Field of Classification Search
None
See application file for complete search history.

(56) References Cited

U.S. PATENT DOCUMENTS

| | | | | |
|---|---|---|---|---|
| 4,586,510 A | * | 5/1986 | Glaser | A61N 1/36003 482/1 |
| 2008/0288020 A1 | * | 11/2008 | Einav | A61N 1/36003 607/48 |
| 2010/0145236 A1 | * | 6/2010 | Greenberg | A61B 5/1101 600/595 |
| 2010/0179453 A1 | * | 7/2010 | Schweighofer | A61B 5/1118 600/595 |
| 2013/0324868 A1 | * | 12/2013 | Kaib | A61N 1/3937 600/510 |
| 2015/0035857 A1 | * | 2/2015 | Lowe | G09G 5/377 345/629 |
| 2017/0238812 A1 | * | 8/2017 | Atlas | G16H 40/67 |
| 2018/0020969 A1 | * | 1/2018 | Cinquin | A61B 5/11 600/595 |

* cited by examiner

*Primary Examiner* — Erica S Lee

(57) ABSTRACT

According to an aspect, a system for stimulating muscle comprises a set of stimulators to stimulate a first muscles, a set of sensors providing first measurement comprising a set of electromyograms (EMG) from another set of muscles coupled to the body part, a set of sensors mounted in the vicinity of the set of stimulator and the set of sensors, providing a measurement representing a motion and orientation of the first body part, another set of sensors providing a measurement representing a condition external to the body part, a processor generating a first position of the body part at a first time instance from the measurements and a processor adjusting at least one of a time duration, trigger instance, and trigger strength of the set of stimulator. In that, the comparator generates a position error as difference between the first position and a reference.

11 Claims, 14 Drawing Sheets

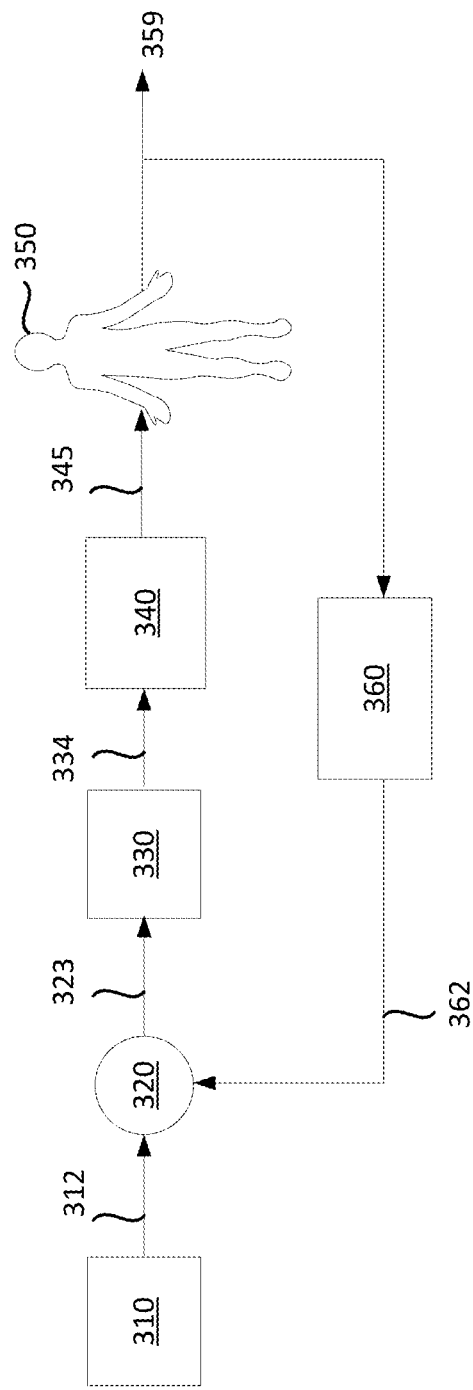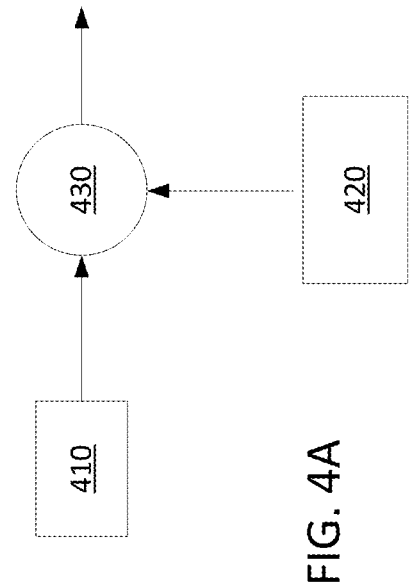

DEVICE, SYSTEM AND APPARATUS FOR FUNCTIONAL ELECTRICAL STIMULATION OF MUSCLE

CROSS REFERENCES TO RELATED APPLICATIONS

This application claims priority from Indian patent application No. 201641004692 filed on Feb. 10, 2016 which is incorporated herein in its entirety by reference.

BACKGROUND

Technical Field

Embodiments of the present disclosure relate generally to medical device and more specifically to a device, system and apparatus for functional electrical stimulation of muscle.

Related Art

The muscles in a person are controlled by electrical signals transmitted by Motor neurons to perform a specific action. In case of person with movement disorder, the muscle(s) is compromised (communication between the muscle fiber and Motor neurons is not active). In order to overcome these muscle disorders, several types of physiotherapies are performed on the person by medical experts to reactivate the lost communication between the nervous system and the muscle fibers. This physical therapy involves lot of time and is not effective in some conditions.

In an another prior technique, a compromised muscle is stimulated by an electrical signal of a known strength to contract and releases the muscle fibers to perform a specific action thereby moving the body or body part of a person with movement disorder. In a conventional technique a functional electrical stimulation (FES) is provided through a stimulator at the site of the compromised muscle or muscle group. The stimulation contracts the appropriate muscle, resulting in movement of the desired body part. Various types of electrical muscle stimulating devices are developed which benefits the muscles to function in their normal way. However, the conventional electrical muscle stimulating devices are bulky in size and are controlled by various switches present on it or by using a remote control through a wired connection.

In one prior technique, the decision as to when the stimulation should be turned on (or off) is determined based on electrical signals transmitted by Motor neurons (measured and extracted as Electromyogram referred to as EMG). In another prior technique, the decision as to when the stimulation should be turned on (or off) is determined from inertial measurement unit referred to as IMU signal.

SUMMARY

According to an aspect, a system for stimulating muscle comprises a set of stimulators to stimulate a first set of muscles within a first body part, a first set of sensors providing first measurement comprising a set of electromyograms (EMG) from a second set of muscles coupled to the first body part, a second set of sensors mounted in the vicinity of the set of stimulator and the first set of sensors, providing a second measurement representing a motion and orientation of the first body part, a third set of sensors providing a third measurement representing a condition external to the body part, a first processor generating a first position of the body part at a first time instance from the first, second, third measurements and a second processor adjusting at least one of a time duration, trigger instance, and trigger strength of the set of stimulator. In that, the a comparator generating a position error as difference between the first position of the body part and a reference position and the second processor adjusting at least one of a time duration, trigger instance, and trigger strength of the set of stimulator to reduce the position error.

According to another aspect, the third set of sensors comprising a set of flex sensors mounted over the first body part to provide a first attitude of the first body part and the first processor generating a drift free attitude from the first attitude and the second measurement. In that, the third set of sensors comprises a set of cameras mounted over a third body part to provide sequence of images and the first processor generating a distance between the first body part and an object in the sequence of images and the first processor is operative to determine a distance between the object and body part in the image frame and to determine orientation of object with respect to the body part in the image frame and the second processor is operative to trigger the set of stimulator with first trigger strength when the distance is within a first reference range and to trigger the set of stimulator with second trigger strength that is greater than the first current value when the distance is within second reference range that is closer to the object. Further, the second processor is further configured to triggering the set of stimulator with third trigger strength when the distance is within a first reference range and the orientation of the object is vertical and trigger the stimulator with fourth trigger strength that is greater than the third current value when the distance is within second reference range and the orientation is vertical.

According to yet another aspect, the system comprises apparel wearable over the first and second body part, in that, the first set of stimulators and the first set of sensors are embedded to make contact with first and second set of muscles when worn.

According to another aspect, the system comprises a reference position generator generating a set of reference positions from the first, second and third measurements and a trajectory generator generating a set intermediate positions between the reference positions. In that, the set of reference positions comprises plurality of gait positions of a limb in a gait cycle and the set intermediary positions comprises the plurality of positions of the limb between two successive gait positions. Further the plurality of positions of the limb between two successive gait positions are determined from at least one of a cadence, stride length, gait speed, balance, and energy consumption in the gait cycle.

According to another aspect, the system further comprises a wireless communication module to transfer and receive information to and from a central server system and a database, in that, the first, second, third measurement, the position error, time duration, trigger instance, and trigger strength are transferred to the database and the plurality of positions of the limb between two successive gait positions, the cadence, stride length, gait speed, balance, and energy consumption in the gait cycle are received from the database.

According to yet another aspect, a method of triggering a functional electric stimulator comprises capturing plurality of image frames, classifying object and body part in the image frames, determining a distance between the object and body part in the image frame, determining orientation of object with respect to the body part in the image frame, triggering the stimulator with first current value when the distance is within a first reference range and triggering the stimulator with second current value greater than the first current value when the distance is within second reference range that is closer to the object.

In an embodiment, the method comprises determining orientation of the object, triggering the stimulator with third current value when the distance is within a first reference range and the orientation is vertical, triggering the stimulator with fourth current value greater than the third current value when the distance is within second reference range and the orientation is vertical.

According to another aspect, a method of stimulating a limb in a gait cycle comprises determining a primary gait characteristic from a first set of measurements, determining a secondary gait characteristics from the primary gait characteristic and the first set of measurements, determining a set of primary limb positions from the primary gait characteristic, determining a plurality of secondary positions representing a trajectory of the limb between the two primary limb positions, providing first set of functional stimulations to position the limb in primary limb position, providing second set of functional stimulations to maintain the limb in the trajectory. In that, the second set function stimulations comprises plurality of triggers spread over a time period between the two primary limb positions in accordance with the secondary gait characteristics. Further, the secondary gait characteristic comprises cadence, stride length, gait speed, balance, and energy consumption and the first set of measurement comprises attitude of the limb, electromyogram (EMG) and sequence images of the limb in an environment.

Several aspects are described below, with reference to diagrams. It should be understood that numerous specific details, relationships, and methods are set forth to provide a full understanding of the present disclosure. One who skilled in the relevant art, however, will readily recognize that the present disclosure can be practiced without one or more of the specific details, or with other methods, etc. In other instances, well-known structures or operations are not shown in detail to avoid obscuring the features of the present disclosure.

BRIEF DESCRIPTION OF DRAWINGS

FIG. 3 is a block diagram of an example EFS system illustrating the manner in which the elements of the EFS system are operative in an embodiment.

FIG. 4A is a block diagram illustrating the manner in which the attitude is estimated in an embodiment.

Figure 12A:
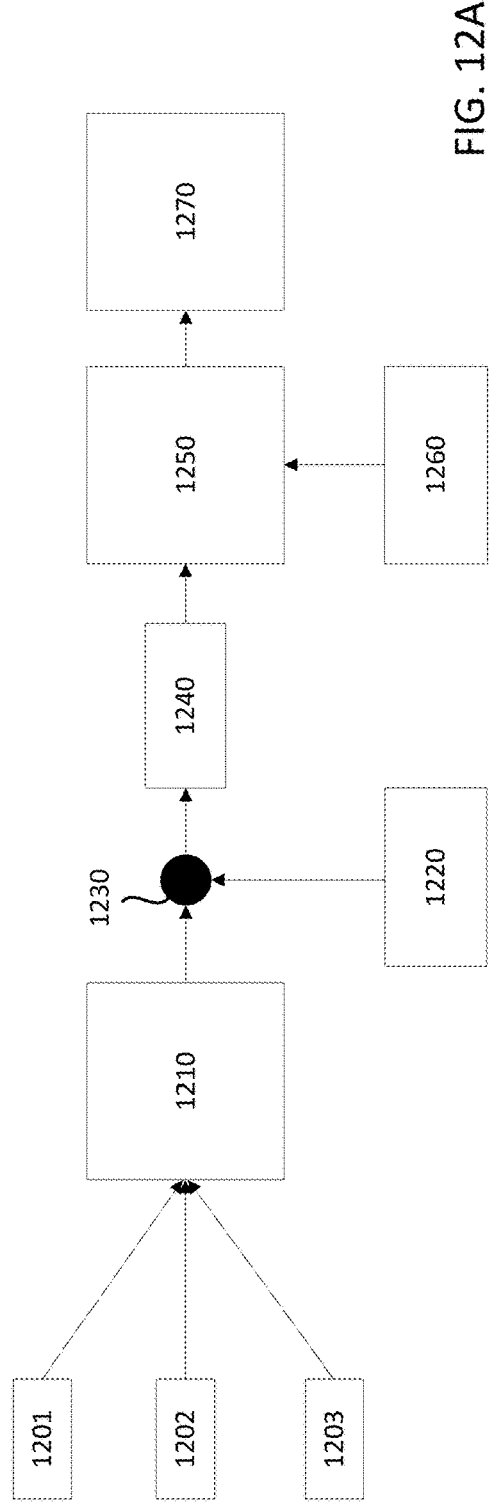
FIG. 12A is a block diagram illustrating the manner in which the machine learning techniques are adapted to detect individual gait characteristics in each gait cycle to trigger the FES at pre-defined parts of the gait cycle.
Figure 12B:
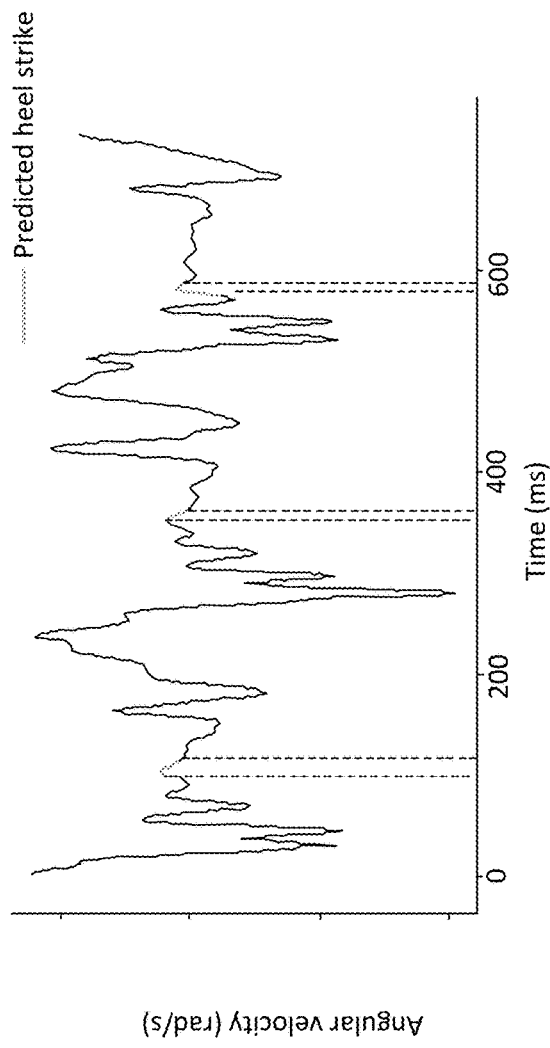

The FIG. 12B is a plot of measurement of angular velocity over number of gait cycle.

Figure 13:
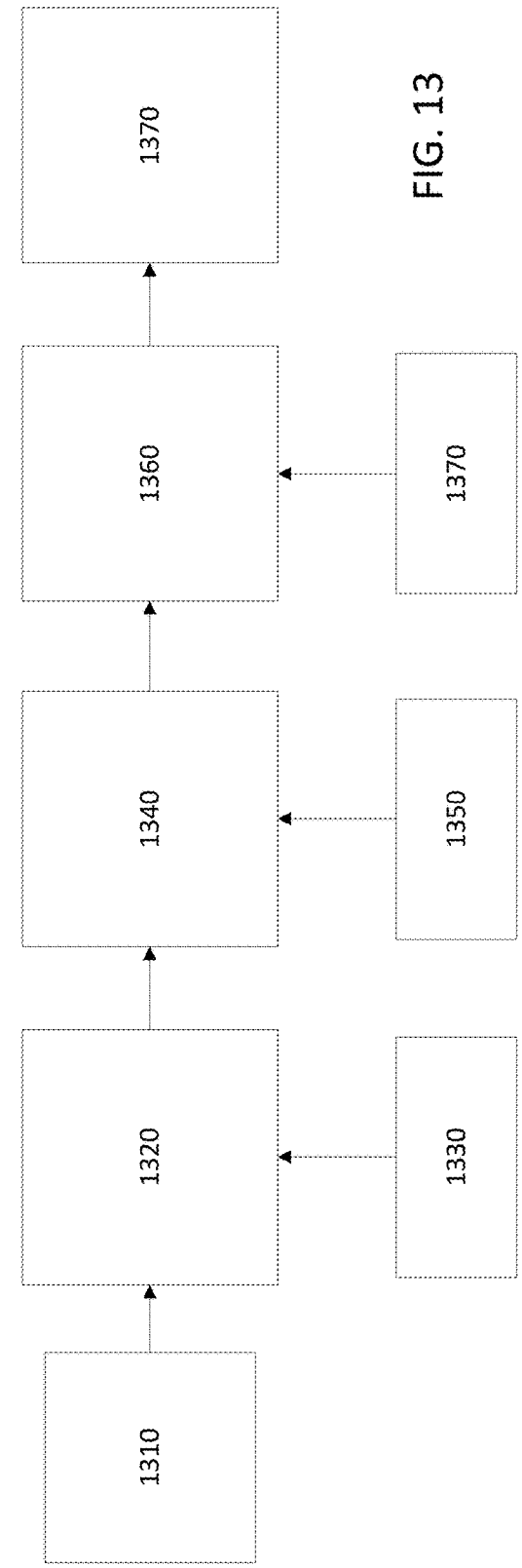

FIG. 13 is a block diagram illustrating the manner in which multiple FES are triggered based on the secondary gait parameters.

Figure 14:
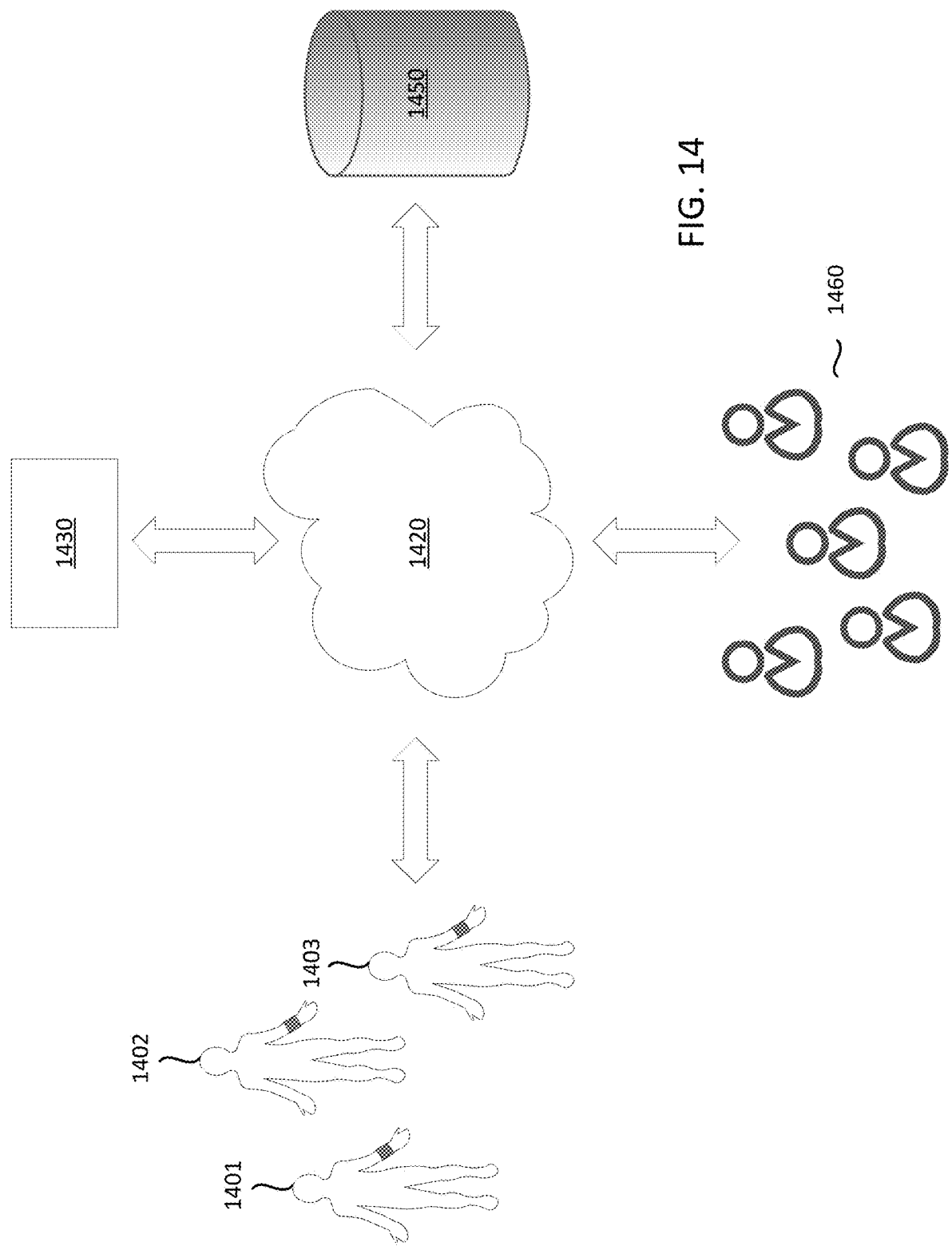

FIG. 14 is the environment in which the various aspect of the present disclosure is operative.

DETAILED DESCRIPTION OF THE PREFERRED EXAMPLES

Figure 1:
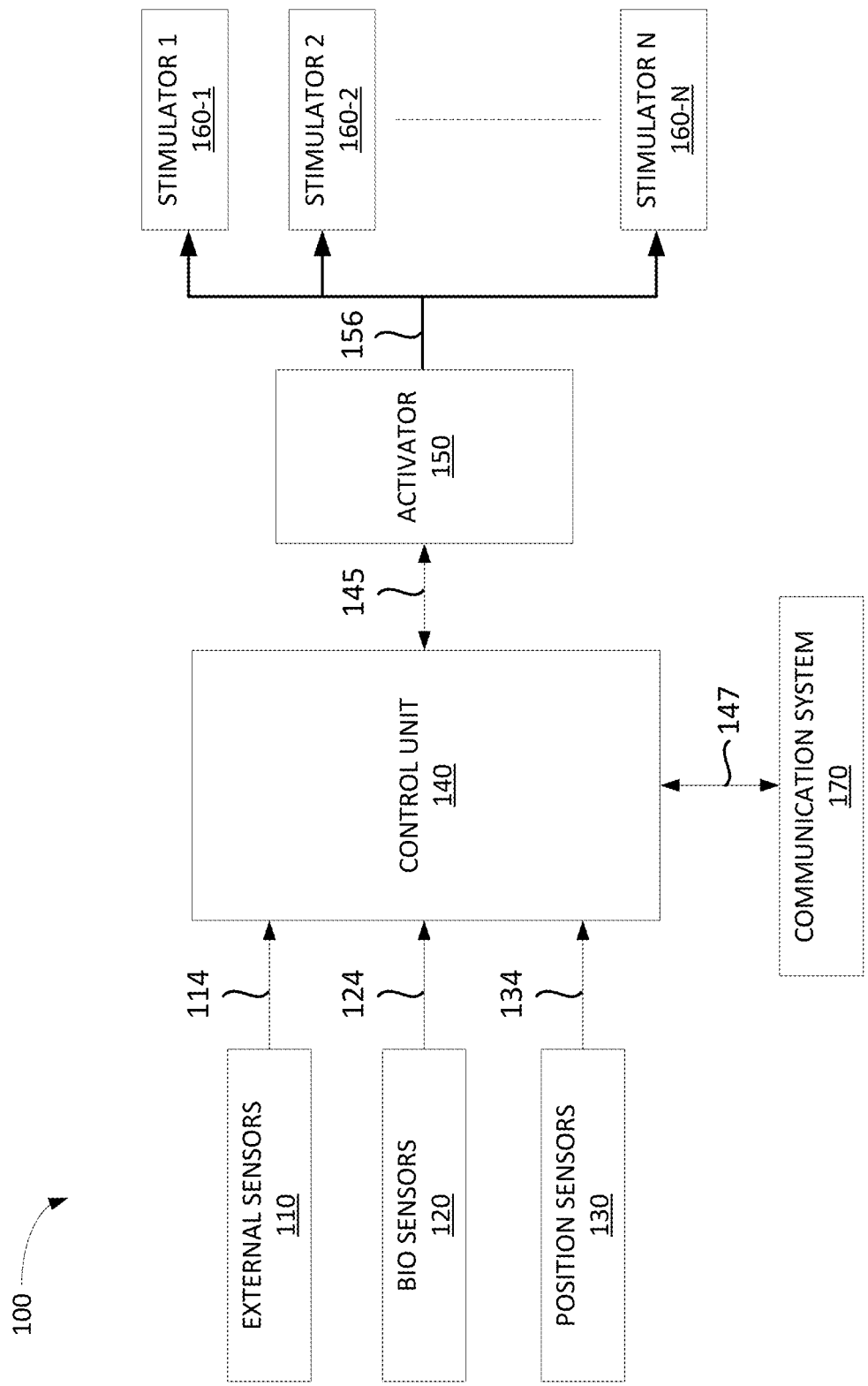
FIG. 1 is an example system for functional electrical stimulation of muscle(s) in an embodiment.

FIG. 1 is an example system 100 for functional electrical stimulation of muscle(s) in an embodiment. The system is shown comprising external sensors 110, bio-sensors 120, position sensors 130, central processor 140, activator 150, stimulators 160-1 through 160-N and communication unit 170. Each block is further described below.

The external sensors 110 sense condition external to the person requiring functional electrical stimulation. The condition external to the person may comprise objects, obstacle and other parameters that when considered may naturally alter the movement of a body or body part. The external sensors 110 may comprise camera, infrared sensors, sound sensors, near field sensors, flex sensor etc. The external sensors 110 may be deployed in plurality to determine the conditions around the person more accurately and stimulate the muscle(s) accordingly.

The bio-sensors 120 sense biological parameters of the person requiring functional electrical stimulation. The biological parameter may comprise electrical activity of heart, Motor neuron signals, electrical activity of brain, heartbeat rate, glucose level, etc. The bio sensors 120 may generate a signal representing the activity of the various organs and health status. The bio sensors 120 may comprise EMG, electroencephalogram (EEG), electrocardiogram (ECG) etc.

The position sensors 130, sense position and motion of the body and/or body part of a person requiring functional electrical stimulation. The position sensor 130 may comprise inertial measurement unit (IMU), geographical position systems (GPS) and other relative position and motion detectors. The IMU may comprise gyroscopes and accelerometers to measure the motion of the body or body part (in particular acceleration and angular velocity respectively).

The IMU and GPS may operate together to provide accurate measurement of the motion of the body or body part(s). Plurality of IMU may be deployed to determine the motion of more than one body parts of the person. In an embodiment, the system 100 further comprises a memory to store information generated from the external sensors 110, bio sensors 120 and the position sensors 130.

The stimulator 160-1 through 160-N injects the electrical signal of a desired strength to the compromised muscle(s) or nerve that control the compromised muscle. The stimulator 160-1 through 160-N may be attached to the location (over the skin, for example) of the compromised muscle. The stimulator 160-1 through 160-N may comprise the probes, the contact pads, or needles that may be suitably positioned or attached to the skin or to the compromised muscle. In an alternative embodiment, the stimulator 160-1 through 160-N may comprise energizer that generate electrical signal of desired strength to cause the muscle to contract. The stimulator may comprise a calibration control to calibrate at least one of the parameters such as electrical signal strength (trigger strength), time duration, trigger instance etc. The stimulator 160-1 through 160-N may comprise a control unit and the probe attached to the control unit. In that the control unit may be positioned suitably at a different location while the probes may be attached to compromised muscle.

The trigger 150 activates the stimulator to cause functional electric stimulating current/voltage to be applied to the compromised muscle. The trigger 150 generates a signal appropriate for the stimulator to understand and stimulate the muscle. The activator 150 may send a control signal to turn on or turn off a particular or set of stimulators 160-1 through 160-N in any specific order or independent. For example, the activator 150 may generate a control signals in a format acceptable to the stimulator. Alternatively, the activator 150 may comprise set of relays to turn on or turn off the stimulator. The activator 150 may activate or send control signals to the stimulators 160-1 through 160-N based on or as per the instruction received from the central processor 140.

The communication channel 170 enables the central processor 140 to transmit and receive data to and from external systems like, central storage, cloud system, server systems etc. The communication channel may comprise, Wi-Fi, LAN, wireless networks, 3G, 4G communication channels and any other known medium of communication adapted to known communication protocols. The path 114, 124, 134, 145 and 156, represent a wired or wireless path adapted to known protocol for transmission and receiving of data/information/signal to and from the central processor 140. For example, the paths 114, 124, 134 and 145 may represents a copper wire, LAN cable, serial communication paths, WiFi, Bluetooth, Zigbee for example.

The central processor 140 receives sensor signals from the external sensors 110, Bio sensors 120, position sensors 130, reference and calibration data through communication channel 170, and determine the manner and the instance (s) at which the functional electrical stimulation must be triggered. Accordingly, the central processor 140 may generate a signal/data indicating the manner and/or instances at which the stimulator 160-1 through 160-N may be activated. The manner in which the sensors and stimulators may be mounted on the body to collect various biological and environmental parameters is further illustrated.

Figure 2C:
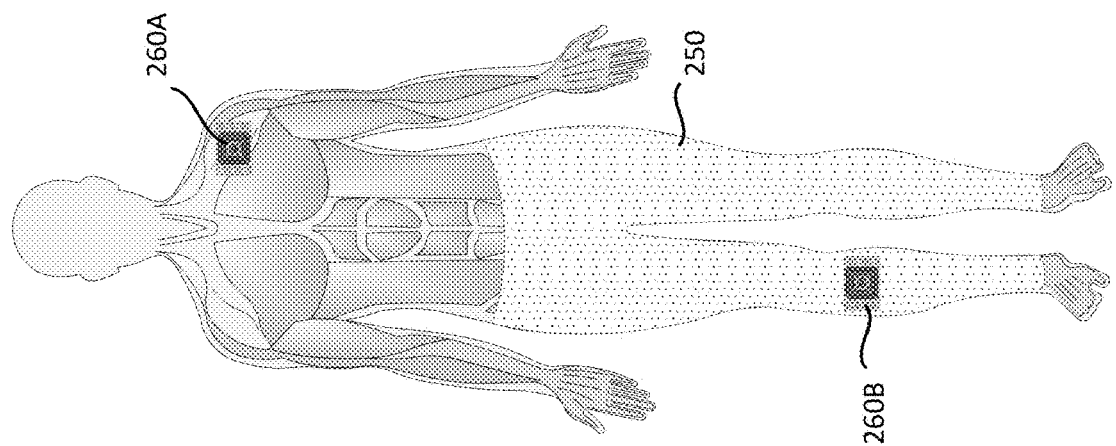
FIGS. 2B and 2C are example wearable apparatus for functional electrical stimulation of muscle in an embodiment.
Figure 2B:
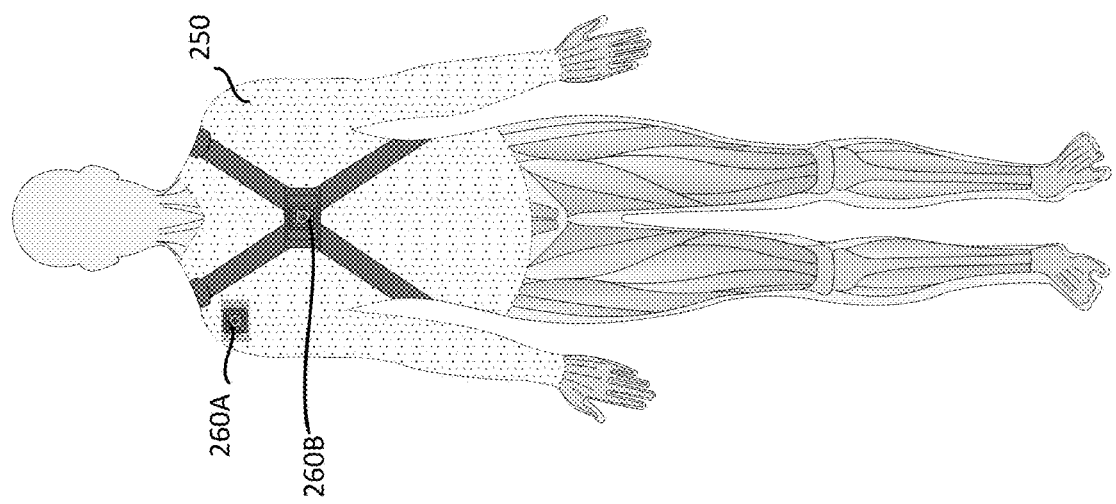
Figure 2A:
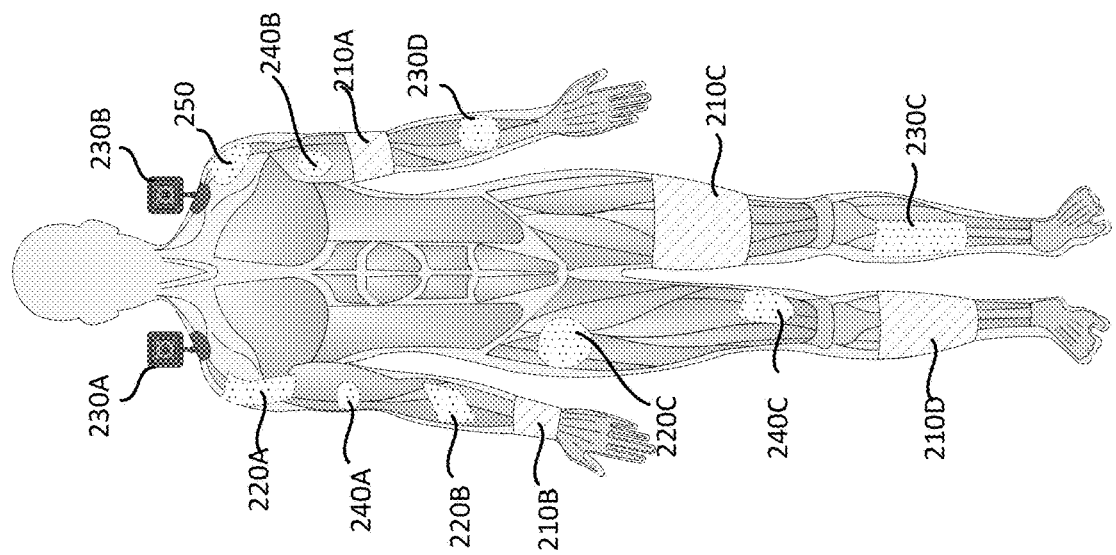
FIG. 2A is an example apparatus for functional electrical stimulation of muscle in an embodiment.

FIG. 2A is an example apparatus for functional electrical stimulation of muscle in an embodiment. The apparatus is shown comprising stimulators 210A through 210D, bio-sensors 220A-220C, external sensors 230A-230D, and Position sensor 240A-240C. Accordingly, sensor information from the bio-sensors 220A-220C (similar to bio-sensors 120), external sensors 230A-230D (similar to external sensor 110) and Position sensor 240A-240C (similar to position sensor 130) are transferred to central processor 140 to determine the trigger instances and manner of stimulating the muscles. The control signal is then sent to the activator 150 to activate the stimulator 210A-210D (similar to stimulator 160-1 through 160-N).

FIGS. 2B and 2C are example wearable apparatus for functional electrical stimulation of muscle in an embodiment. The apparatus is shown comprising wearable part 250, external sensors 260A-260B. In that the stimulators 210A through 210D, bio-sensors 220A-220C, external sensors 230C-230D, and position sensor 240A-240C are mounted or embedded within the wearable part 250 such that when the wearable part 250 is worn on the body, the stimulators make contact with the muscle that are compromised. The wearable part may be constructed to fit and hold the stimulator at the appropriate position and also may indicate the error if the stimulators are not making contact with the desired muscle part. Similarly, the wearable part may house bio sensors and position sensors as well. The wearable part may be a jacket or sleeves, anklets, sock etc. in particular, the illustrated apparatus in FIG. 2B may be employed for disorders in the upper part of the body. While the apparatus in FIG. 2C may be employed for disorders in the lower part of the body. The wearable part 250 in general and external sensors 260A-260B. In that the stimulators 210A through 210D, bio-sensors 220A-220C, external sensors 230C-230D, and position sensor 240A-240C in particular may establish communication with central processor 140 (not shown), activator 150 through wireless paths 114, 124, 134, 145 and 156. Thus, the central processor and the activator may control and activate the stimulator. The manner in which the sensors, central processor and stimulators may be operative in an embodiment is further described below.

FIG. 3 is a block diagram of an example EFS system illustrating the manner in which the elements of the EFS system are operative in an embodiment. The system is shown comprising reference trajectory source 310, comparator 320, optimal FES trigger generator 330, stimulator 340, and sensors 350, and pre-processor 360. Each block is further described below.

The sensors 350 generate set of measurement data and comprises external sensors 110, bio-sensors 120, position sensors 130, and sensors mounted within the wearable part 250. In one embodiment, the measurement data comprises accelerations "a", angular rotation "ω", the local magnetic field "μ", EMG measurements such as muscle activations "$v_m$" measured at one or more locations on the body, flex sensors measurement (from one or more flex sensors) representing bend angles in the corresponding one or more reference angles, and Camera/Ranging sensor measurements such as combination of mono and stereo images, color and IR, laser or LED or radar based ranging images etc.

In one embodiment, the accelerations "a" comprise three dimensional acceleration of a body/body part. The three dimensional acceleration thus measured in x, y and z direction is represented as $a=[a_x,a_y,a_z]$. Similarly, the angular rotation "ω" comprises three dimensional the angular rotation of a body/body part. The three dimensional angular rotation thus measured in x, y and z direction is represented as $\omega=[\omega_x,\omega_y,\omega_z]$. The three dimensional local magnetic field measured along three axis magnetometer may be represented as $\mu=[\mu_x,\mu_y,\mu_z]$. The three dimensional flex sensors provide bending angles in three dimensions and the three dimension flex bending angles are represented as [$\psi_{flex}, \theta_{flex}, \varphi_{flex}$]. The measurement data may be time tagged and packetized for sending over path 359. Further, the measurements data may comprise the information of the body part the sensor is attached to. For example the information may comprise name or identification of the body part like limb, forearm, wrist etc.

The pre-processor 360 receives measurement data on path 359 and generate an estimated position, orientation and direction of the movement of the desired body or body parts (hereafter estimate). The preprocessor 360 may receive additional information from the central database or cloud system to generate the estimate. In one embodiment, the pre-processor 360 perform multiple levels of computations. For example, the pre-processor 360 may estimate the attitude (or 3D orientation) of body part (for example limb) and/or estimate the entire muscle pathways (for example, wrist and upper arm) involved in making a specific motion. In one embodiment pre-processor 360, estimate how the body part interacts with the external environment. The estimate is provided on path 362.

The reference trajectory source 310 provides a set of reference trajectory(ies) that is generally treated as optimal for the particular part of the body to perform an action. For example, the reference trajectory may be desired or optimal movement of the body between two points in space to achieve a predetermined task. The trajectory may comprise specific point in a movement (for example heel strike or heel off point of a gait) and/or an optimal biomechanical body part (like limb) trajectory (points/position in the space) between two reference points like initial and final point. In one embodiment, the reference trajectory source 310 generates the trajectory based on the intent determined from the measurement from one or more sensors. The reference trajectory is provided on path 312.

The comparator 320 computes the deviation of the actual trajectories from the reference trajectories of a desired body part. The comparator receives the reference trajectory and the estimate on path 312 and 262 respectively to compute the deviation (difference signal). The difference signal represents the difference in actual motion and desired motion but not limited to the difference in the attitude of the estimate received on path 362 and the reference points of a body part received on path 312 at a given time. In other words, the deviation may represent the temporal and spatial relationship. The difference signal is provided on path 323.

The optimal FES trigger generator 330 generates a control signal to trigger the stimulators (FES) with specific current ratings. The control signal may comprise information pertaining to time instant for stimulation (time duration), strength of the stimulation current or voltage (trigger strength), sequence and order of stimulator to be activated (trigger instance), duration of stimulation for example. The generator 330 generates optimal trigger points to assist multiple characteristics of the movement of the body part (like gait cycle). The trigger points are generated based on the deviation received on path 323. The control signal is provided on path 334 to one or more stimulators.

The stimulator 340 receives the control signal on path 334 and provides FES to one or more muscle(s), muscle fiber or nerve controlling the muscle. The stimulator 340 may comprise set of stimulator connected to path 334.

In one embodiment, the reference trajectory source 310, comparator 320, optimal FES trigger generator 330 and pre-processor 360 are deployed within the central processor 140. The stimulator 340 comprise stimulator 160-1 through 160-N and the sensors 350 comprises sensors 110, 120, 130.

In an alternative embodiment, the optimal FES trigger generator 330 may be deployed as part of the activator 150. The manner in which the pre-processor 360 may determine the attitude in an embodiment is further described below.

Figure 4B:
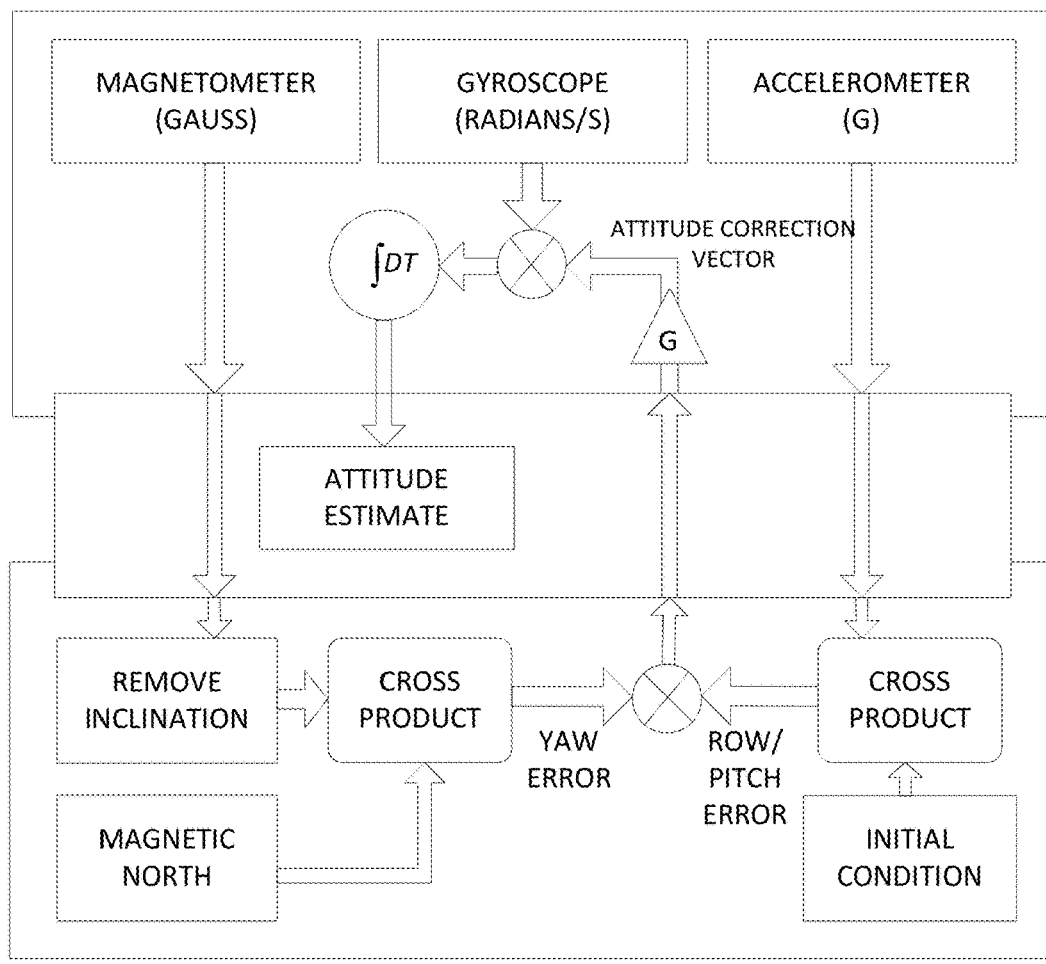
FIG. 4B is an example complimentary filter with (usual notation provided therein) generating attitude [ψ_IMU, θ_IMU, φ_IMU] from IMU raw measurement α, ω and μ.

FIG. 4A is a block diagram illustrating the manner in which the attitude is estimated in an embodiment. The block diagram is shown comprising the IMU attitude computing unit 410, flex sensor attitude computing unit 420, and attitude correction unit 430. The IMU attitude computing unit 410 receive the IMU measurements a=[$a_x, a_y, a_z$], $\omega$=[$\omega_x, \omega_y, \omega_z$] and $\mu$=[$\mu_x, \mu_y, \mu_z$] and generate IMU attitude [$\psi_{IMU}, \theta_{IMU}, \varphi_{IMU}$]. The flex sensor attitude computing unit 420 receives flex bending angles and generate flex attitude [$\psi_{flex}, \theta_{flex}, \varphi_{flex}$]. The attitude correction unit 430 receives the IMU attitude and flex attitude and generate a drift corrected on path 434. For example, when the difference between the IMU and the flex attitude is greater than a threshold value, the correction unit 430 may correct and adjust the reference value in the IMU attitude computing unit 410. In an alternative embodiment, the IMU attitude computing unit may be provided with the error signal to correct the drift in the attitude computation. FIG. 4B is an example complimentary filter with (usual notation provided therein) generating attitude [$\psi_{IMU}, \theta_{IMU}, \varphi_{IMU}$] from IMU raw measurement $\alpha$, $\omega$ and $\mu$. Thus, the flex sensor mounted in the proximity of the IMU on a body part is effectively used to determine the attitude with a reduced drift (with higher accuracy). The drift corrected attitude $\hat{\psi}$, $\hat{\theta}$, $\hat{\varphi}$ may be provided on path 362. Additionally the preprocessor may determine the intent movement from the biosensors and provide the intent move on path 362. The manner in which the pre-processor 360 may determine the intent is further described below.

In one embodiment, the pre-processor 360 takes advantage of the fact that the motion of an end effectors (movement of a body part like hand, finger leg) generally follows specific pathways in the muscle network. In other words, the decision to move a part of the body to perform an action is cognitive and brain may activate series of muscles to finally cause the movement of the desired body part. Accordingly, the pre-processor is configured to determine the desired movement (intent) of a body part based on the series of muscle activation signal received from bio-sensors.

Figure 5:
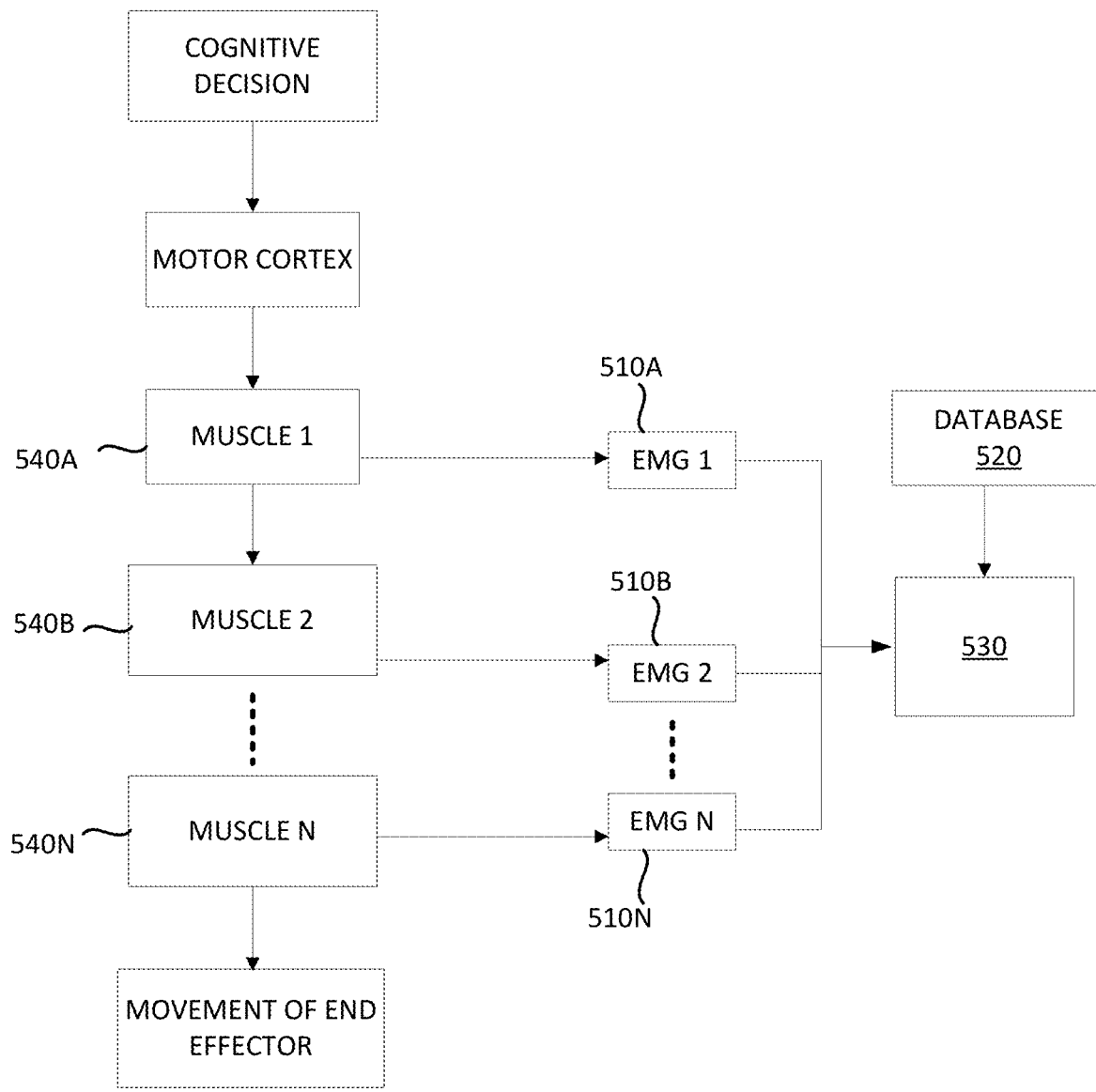
FIG. 5 is a block diagram illustrating the manner in which the pre-processor may be deployed to determine the intent.

FIG. 5 is a block diagram illustrating the manner in which the pre-processor may be deployed to determine the intent. The block diagram is shown comprising EMG 510A-510N, database 520, and end effect detector 530. In that the EMG 510A through 510N is shown coupled to corresponding muscles 540A through 540N.

The database 520 stores muscle pathways and corresponding end effector as a reference. The muscle pathways are the set of EMG signals received from the corresponding set of muscles. Further, the muscle pathway may also comprise the order and time information of the set of EMG signals. In one embodiment, the database is iteratively updated to hold the muscle pathways and corresponding end effector. For example, the muscle pathways sensed from the EMG 510A-510N and the corresponding end effector sensed from sensors 110, 120 and 130 (for example IMU and flex sensors) are constantly updated, added, deleted. In an alternative embodiment, an iterative learning is deployed to map muscle pathways to the effector motion.

The EMG 510A through 510N captures electrical signal from the muscles 540A through 540N respectively. The captured electrical signal is passed to the end effect detector 530. The end effect detector 530 compares the received EMG signal pattern in the data base to determine the intent (end motion). The intent is provided on the path 362 for activation or stimulation of the corresponding body part.

In one embodiment, the pre-processor 360 determine the temporal and spatial relation between the object(s) and the desired body part in the environment. The external sensors 110 data is employed for detecting the object(s), body part and a temporal relation between them. The external sensors like camera, infrared, radar sensors, 3D image sensing equipments are employed. In case of 3D image detection multiple cameras strategically positioned to determine the 3D spatial relation are employed. In another embodiment, cameras/ranging sensors are placed/mounted on the desired body or in the external environment. The stimulators are activated based on the temporal and spatial relation determined. The manner in which the temporal and spatial relation is determined in an embodiment is further described below.

Figure 6:
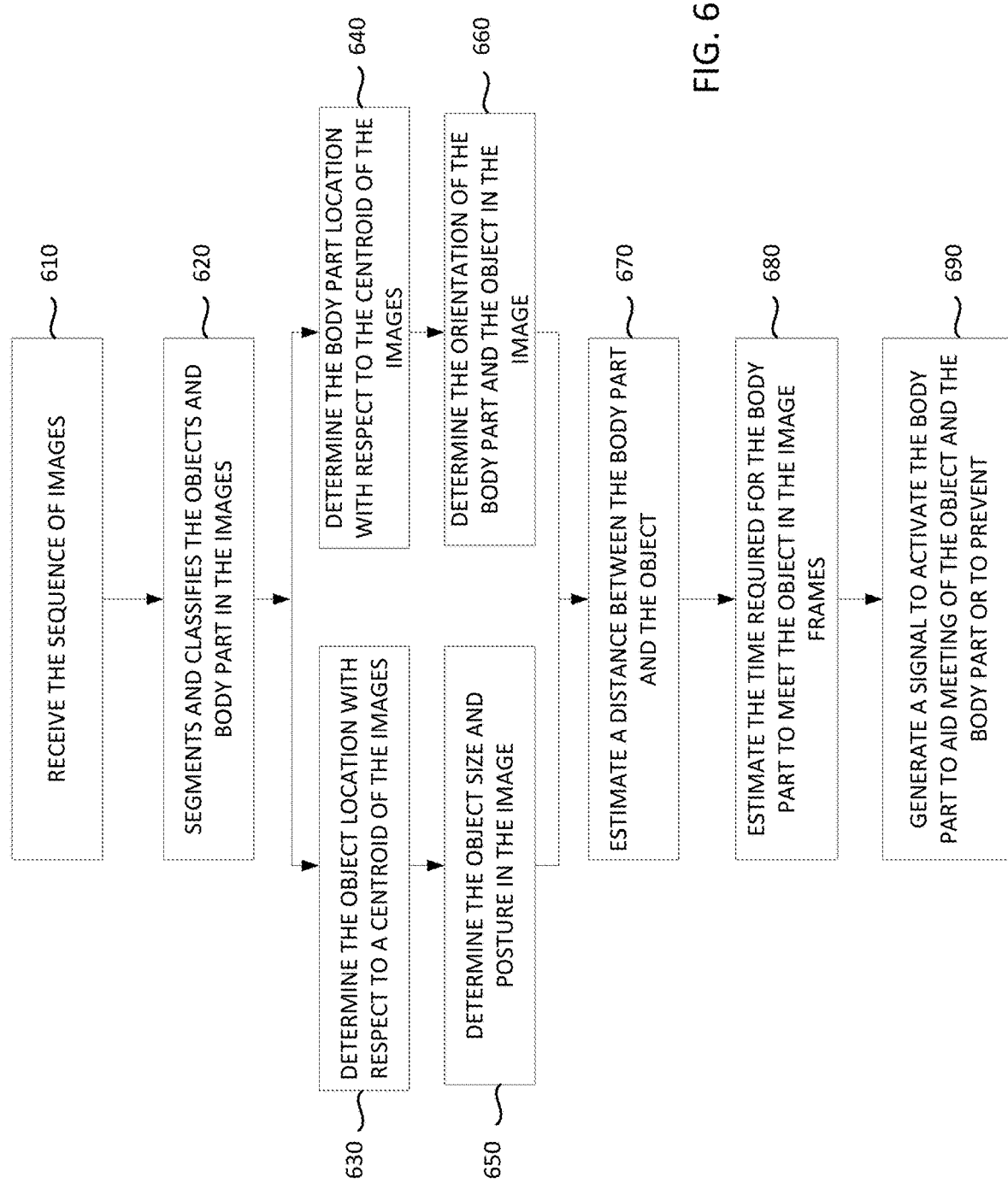
FIG. 6 is a block diagram illustrating the manner in which the pre-processor determine temporal and spatial relation between an object and body part in an embodiment.

FIG. 6 is a block diagram illustrating the manner in which the pre-processor determine temporal and spatial relation between an object and body part in an embodiment. In block 610, the pre-processor receive the sequence of images captured from one or more cameras placed/mounted in the vicinity of the body part. The images may be received as frames of a video with a definite time intervals.

In block 620, the pre-processor segments and classifies the objects and body part in the images or image frames (sequence). The detection and classification of objects and the body part may be performed in any known way. In one embodiment, the detection and classification of objects and the body part is determined by first segmenting the image, extracting the objects in the image and classification of the extracted object is performed by comparing the extracted object with the known objects and body part in the database. The object properties, like color, texture, shape, position are provided to the block 630 and 640.

In block 630, the pre-processor determine the object location with respect to a centroid of the images. The preprocessor may determine object location with reference to the periphery of the object and/or with reference to the centroid of the object. Similarly in block 640, the pre-processor determine the body part location with respect to the centroid of the images.

In block 650, the pre-processor determine the object size and posture in the image. The size may be determined based on the estimated scale and known object measurements stored in the database. Any other known technique maybe deployed to determined the size and posture of the object. For example, the linearity, contour, balancing point, etc may be determined as part of the posture of the object. In block 660, the pre-processor determine the orientation of the body part and the object in the image. For example, the orientation of the body part in relation to the posture of the object may be determined. For example, the vertically standing object, horizontally laid object, orientation of body part ad horizontal, vertical, suitable, not suitable etc., may be determined.

In block 670, the preprocessor estimate a distance between the body part and the object. The distance between the body part and the object may be computed between the peripherals or between the centroids. In block 680, the preprocessor estimate the time required for the body part to meet the object in the image frames. The increase or decrease in the distance computed in block 670 for number of frames may be used to determine the time for the distance to become zero. The time required for distance to become zero and the relative orientation of the body part and posture of the object is provided to the block 690.

In block 690, the preprocessor generate a signal to activate the body part to aid meeting of the object and the body part or to prevent the meeting of the body part with the object. The generated signal is provided on the path 362. Accordingly, the estimate data provided on path 362 comprise the attitude, the intent, and the spatial and temporal relation of the body part and the object. The manner in which the reference trajectory source 310 generates various references is further described below.

Figure 7:
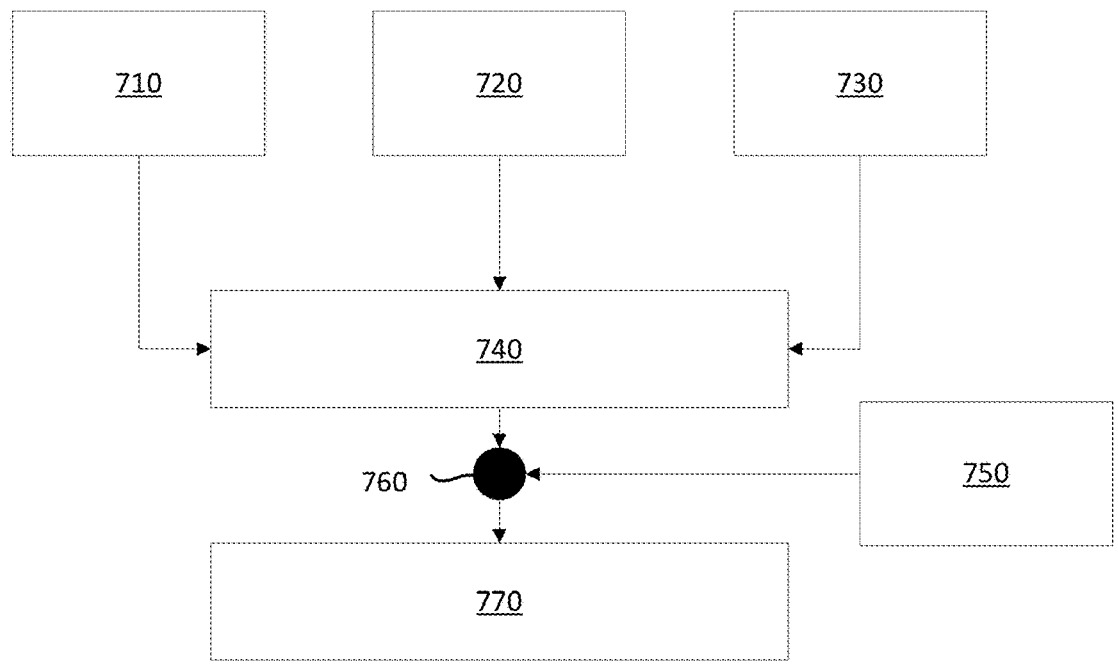
FIG. 7 is a block diagram illustrating the manner in which the specific reference points are determined in an embodiment.

FIG. 7 is a block diagram illustrating the manner in which the specific reference points are determined (reference position generator) in an embodiment. In that, the block 710 provides IMU measurement of the body part. The block 710, may represent IMU in the sensors 340. The block 720 provides EMG signal from the plurality of the muscles. The block 720 may represent the EMG 510A-510N. The block 730 provides images or sequence of images from one or more cameras. In block 740, the attitude, pathways, temporal and spatial relation is determined as described in the sections above. In block 750, the iterative machine learning techniques with known movements (say, gait cycle) is stored for reference. In block 760, the iterative machine learning technique is applied to the attitude, pathways, temporal and spatial relation. In block 770, the specific points of interest (like heel strike, etc) are extracted. The extracted reference points are provided for comparison on path 312. In an alternative embodiment, in addition to the reference points, complete trajectory points from the intent detection is provided as reference.

Figure 8:
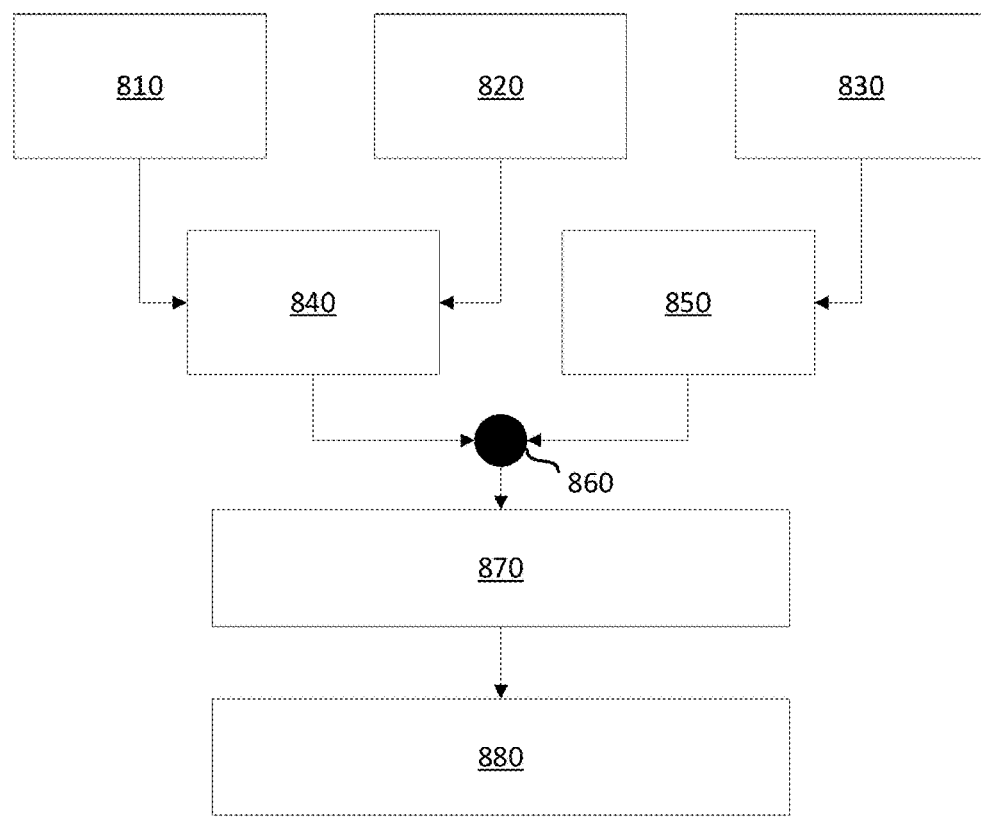
FIG. 8 is a block diagram illustrating the manner in which the complete trajectory reference may be generated.

FIG. 8 is a block diagram illustrating the manner in which the complete trajectory reference may be generated (trajectory generator). The block 810, 820, and 830 operate similar to 710, 720 and 730. In the block 840, attitude and muscle pathway is determined using the techniques described above. In block 850, object location, body part location and the other properties of the image are determined. In block 860, attitude and muscle pathway, object location, body part location and image properties are combined together (packetized) and provided to block 870. In Block 870, an initial and final point in the spatial trajectory is computed. In block 880, optimal path between initial position and the final position and spatial interaction point with object is generated. The complete trajectories with interaction points are provided on path 312 for comparison and determining the stimulation points, sequence and stimulation strength. Accordingly, the reference trajectory may begin with a known preset values and may be updated time to time (iteratively) based on the measurements. Thus, the estimate on path 362 is ahead in time at least by one time unit compared to reference values on 312. Manner in which the, the stimulation is adaptively changed based on spatial and temporal conditions is further described below with an example.

Figure 9D:
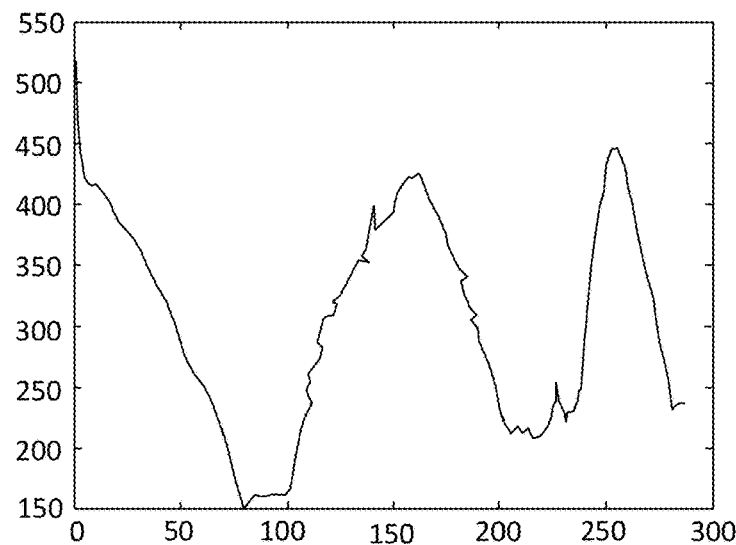
FIG. 9D is an example plot of pixel distance variation as the limb move towards and away from the object on multiple instances.
Figure 9A:
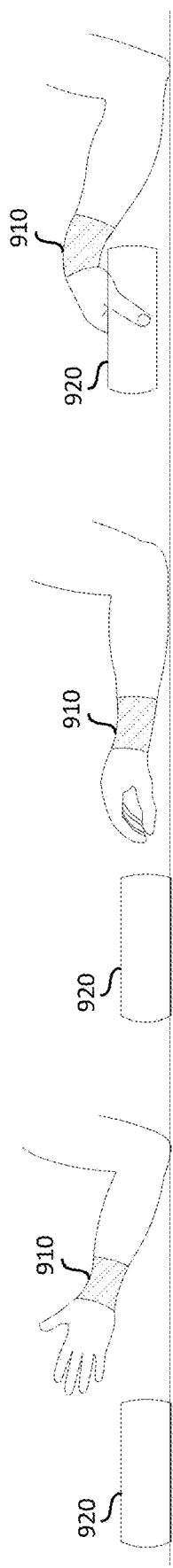
FIG. 9A is a sketch illustrating an example scenario of a limb (hand) 910 desiring to pick an object 920.
Figure 9B:
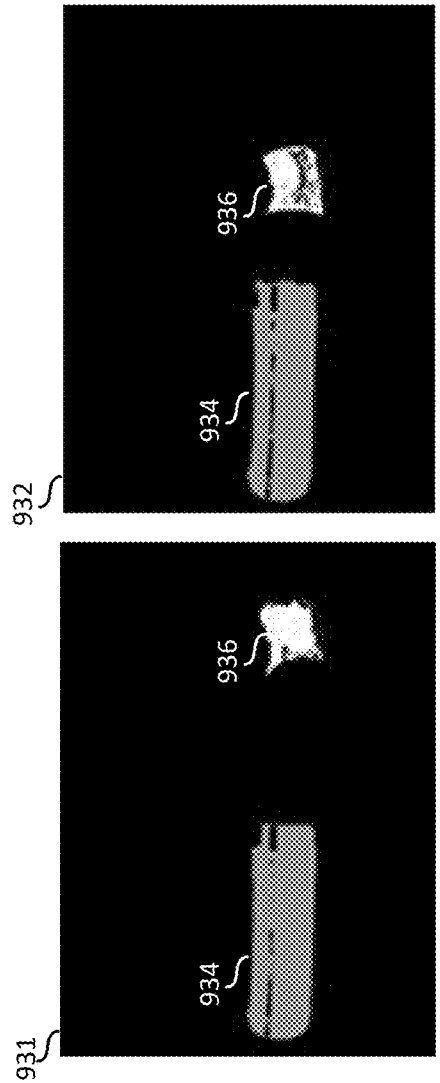
FIG. 9B is example set of images captured from the external sensor (CAMERA) positioned appropriately to capture the scene.

FIG. 9A is a sketch illustrating an example scenario of a limb (hand) 910 desiring to pick an object 920. In that the 921 represents the stimulator and sensors mounted on the wrist for stimulating appropriate muscle. FIG. 9B is example set of images captured from the external sensor (CAMERA) positioned appropriately to capture the scene. In that, images 931 and 932 are the processed images to represent only the identified object 934 and the body part (limb) 936 (in particular the part 921).

Figure 9C:
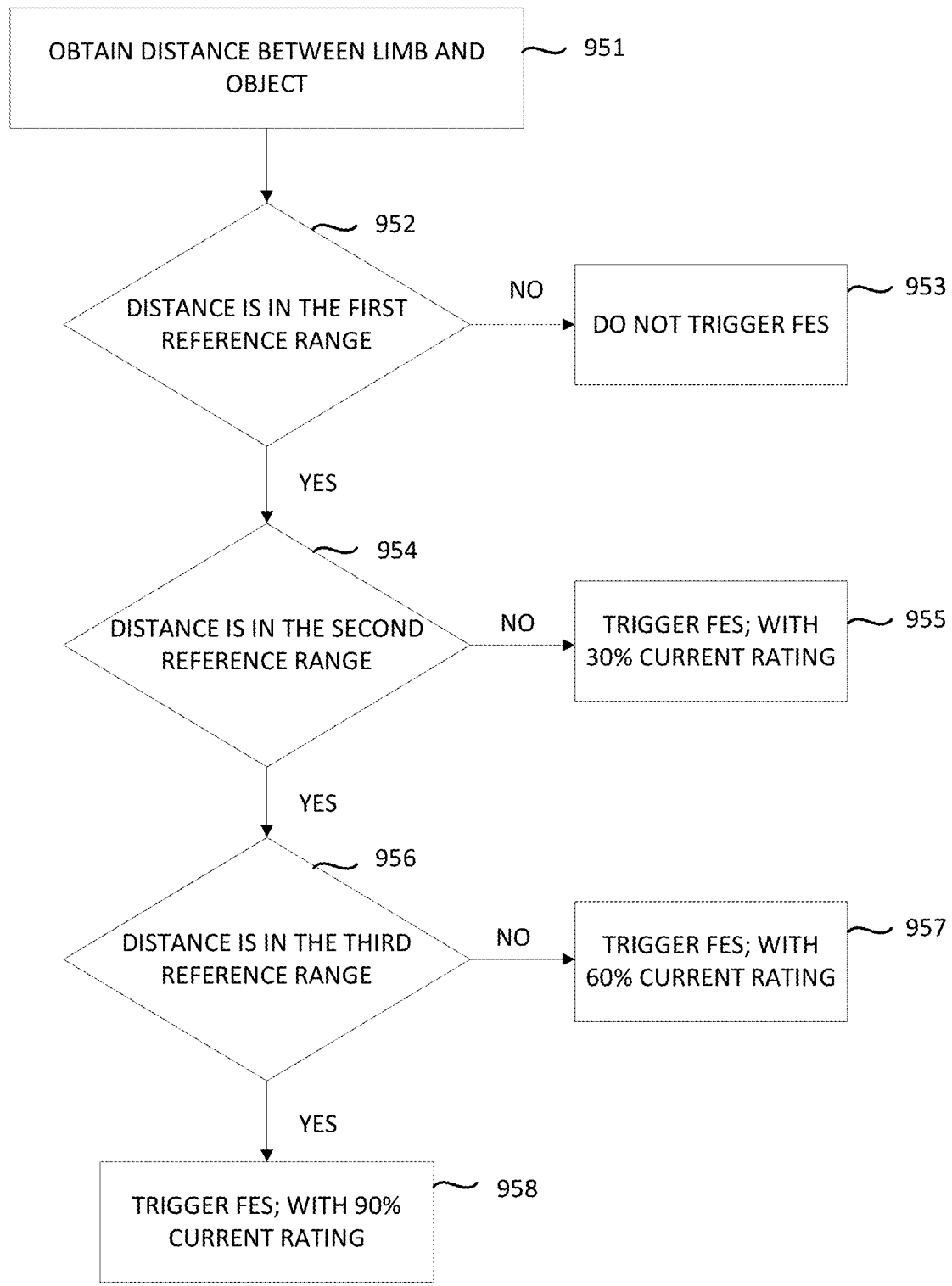
FIG. 9C is a block diagram illustrating a manner in which the stimulator may be activated based on the spatial relation.

FIG. 9C is a block diagram illustrating a manner in which the stimulator may be activated based on the spatial relation. In block 951, the central processor determines distance between limb 936 and object 934. The distance may be computed in terms of the number of pixels between the center of the object 934 and center of the limb 936. Alternatively, the distance may be computed between the closest boundary forming the object image 934 and the limb image 936. An example plot of pixel distance variation as the limb move towards and away from the object on multiple instances is represented in FIG. 9D. In another embodiment, a stereo camera or a ranging sensor (LIDAR, RADAR etc) is used to determine true spatial distance.

In block 952, the central processor checks if the distance between limb 936 and object 934 is in the first range of value. The first range of value may comprise a distance greater than a first threshold value. If the condition returns true then the control passes to block 954, else to block 953. In block 953, the central processor performs no action or the stimulators are not triggered. The range value may be selected and set in the plot FIG. 9D In block 954, the central processor checks if the distance between limb 936 and object 934 is in the second range of value. The second range of value may comprise a distance less than the first threshold and greater than a second threshold value. If the condition returns true then the control passes to block 956, else to block 955. In block 955, the central processor triggers the stimulator with a first electric signal strength. For example, the processor may send a control signal to the activator to stimulate the muscle with a 30% current rating (the desired maximum current that may be applied or the current rating of the stimulator device).

In block 956, the central processor checks if the distance between limb 936 and object 934 is in the third range of value. The third range of value may comprise a distance less than the second threshold and greater than a third threshold value. If the condition returns true then the control passes to block 958, else to block 957. In block 957, the central processor triggers the stimulator with second electric signal strength. For example, the processor may send a control signal to the activator to stimulate the muscle with a 60% current rating.

In block 958, the central processor triggers the stimulator with larger electric signal strength. For example, the processor may send a control signal to the activator to stimulate the muscle with a 90% current rating. Accordingly, four threshold conditions are mapped to a different current requirement from the FES. Thus as the body part (wrist) gets closer to the object (which it intends to grasp) the current increases. The current required can be modified to suit precise biomechanical and energy requirements. In an alternative embodiment, triggering stimulator is adjusted based on the temporal conditions identified from the sequence of the image.

Figure 10A:
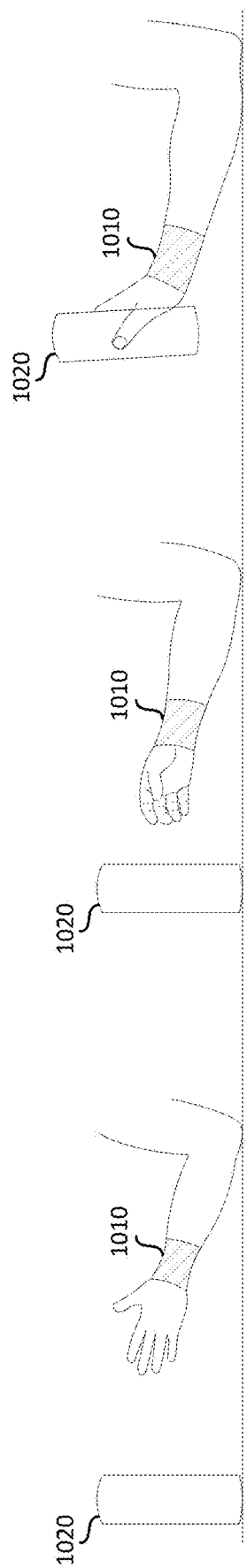
FIG. 10A is a sketch illustrating an example scenario of a limb (hand) 1010 desiring to pick an object 1020 that is standing vertical (relative orientation).
Figure 10B:
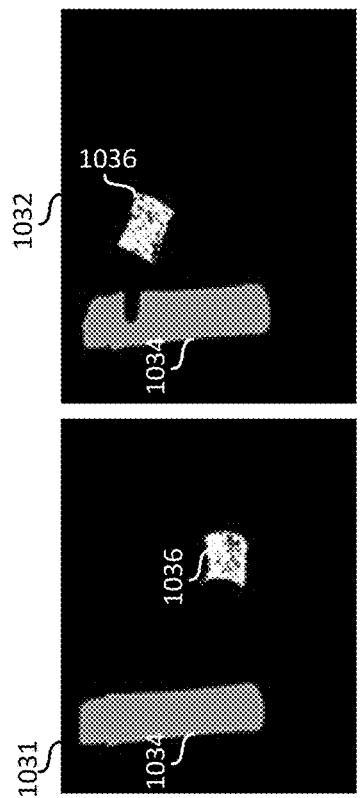
FIG. 10B is example set of images captured from the external sensor (CAMERA) positioned appropriately to capture the scene.

In another embodiment, the orientation and size of an object with respect to a subject, influences the triggering mechanism. FIG. 10A is a sketch illustrating an example scenario of a limb (hand) 1010 desiring to pick an object 1020 that is standing vertical (relative orientation). In that the 1021 represents the stimulator and sensors mounted on the wrist for stimulating appropriate muscle. FIG. 10B is example set of images captured from the external sensor (CAMERA) positioned appropriately to capture the scene. In that, images 1031 and 1032 are the processed images to represent only the identified object 1034 and the body part (limb) 1036 (in particular the part 1021).

Figure 10C:
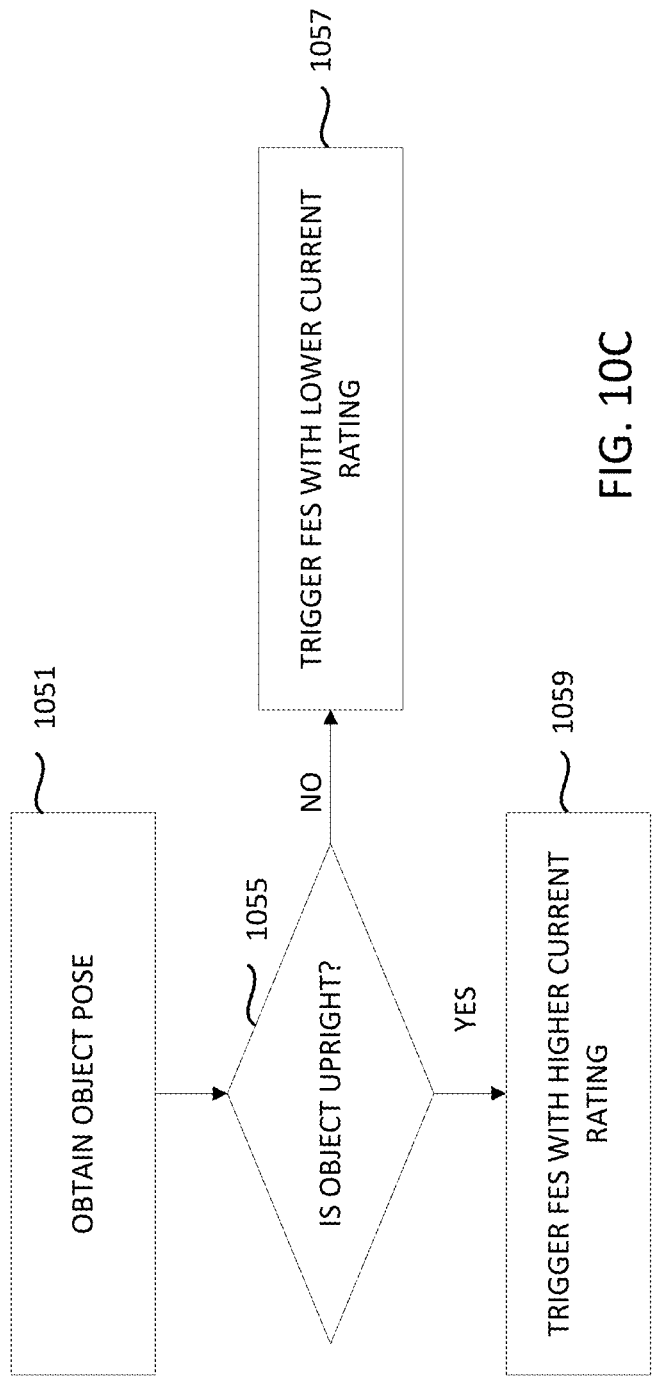
FIG. 10C is a block diagram illustrating a manner in which the stimulator may be activated based on the temporal relation.

FIG. 10C is a block diagram illustrating a manner in which the stimulator may be activated based on the temporal relation. In block 1051, the central processor determines the posture of the object 1034. The posture may be determined as vertical or horizontal (upright or lying). In block 1055, the central processor checks if the object is upright. If the condition returns true then the control passes to block 1059, else to block 1057. In block 1057, the central processor triggers the stimulator with low signal strength. For example, the processor may send a control signal to the activator to stimulate the muscle with a 30% current rating. In block 1059, the central processor triggers the stimulator with larger electric signal strength. For example, the processor may send a control signal to the activator to stimulate the muscle with a 90% current rating as larger current may be required to rotate the wrist (assuming the wrist is compromised). In an alternative embodiment, the processor may trigger additional set of stimulator to cause the rotation required to hold an upright object. Thus, the stimulators are triggered in consideration to distance, orientation and size of the object to ease the completion of task.

In one embodiment, the attitude information computed using the IMUs and the EMG information obtained from the analog circuit are combined. The limb angular position may be used as a failsafe mechanism. For example, the stimulator may not be turned on when the limb is not in an appropriate position even if the EMG shows desired activity. The EMG signals are calibrated (with subject at a pre-defined position), during motion (of the limb) if the measured EMG signal exceeds a predefined threshold and the limb angular position is satisfied as measured by the IMU the FES is triggered. Similarly, the technique may be extended to the detection of multiple muscle signals. The FES may be triggered only when a pre-defined pattern (of multiple muscle activation and limb joint positions) is detected.

The manner in which multiple FES trigger points are determined and the multiple FES is triggered is further described with reference to gait cycle. In that the multiple FES are triggered to assist multiple characteristics of a gait/movement cycle.

Figure 11:
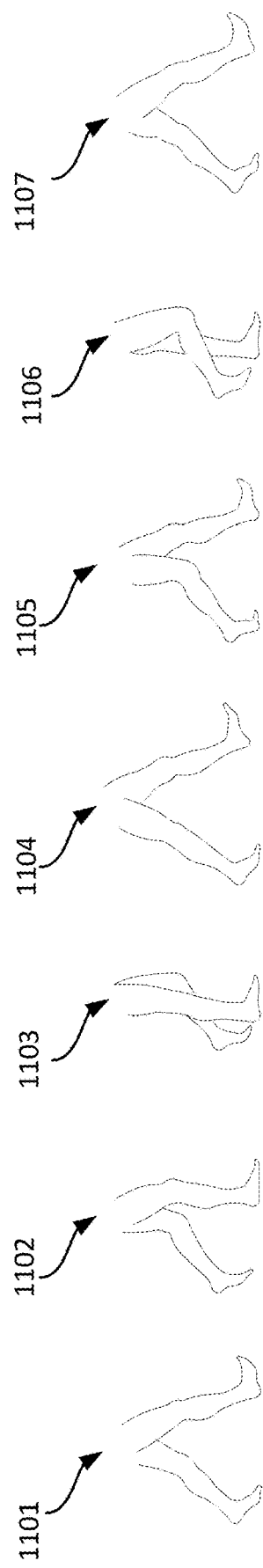
FIG. 11 is a sketch illustrating a gait cycle.

FIG. 11 is a sketch illustrating a gait cycle. As shown there the gait cycle comprises primary characteristics such as heel strike 1101, foot flat 1102, mid stance 1103, heel off 1104, toe off 1105, mid swing 1106, and terminal swing 1107 as well known in the art. The secondary characteristic of the gate cycle comprises, parameter such as cadence, stride length, speed, for example.

FIG. 12A is a block diagram illustrating the manner in which the machine learning techniques are adapted to detect individual gait characteristics in each gait cycle to trigger the FES at pre-defined parts of the gait cycle. In that, blocks 1201, 1202, and 1203 respectively provide IMU measurement, EMG signal and camera images. In block 1210, the central processor determines the attitude, muscle pathways, and temporal/spatial relation as described in sections above. In block 1220, a known machine learning algorithm is deployed. In block 1230, the attitude, muscle pathways, and temporal/spatial and the machine learning algorithm is combined together and provided to block 1240 that determine the gait. In block 1250, the individual gait characteristic is extracted from the gait received from block 1240. The gait characteristic may be extracted with reference to object properties stored in database 1260. FIG. 12B illustrates an example determination of a one of the characteristic (heal strike) in en embodiment. The FIG. 12B is a plot of measurement of angular velocity over number of gait cycle. The region starting with substantially zero angular velocity may be determined as heal strike point. In block 1270, the FES is triggered across the predefined individual gait positions.

The manner in which the system automatically detects secondary gait parameters such as cadence, stride length, gait speed, balance, energy consumption etc and triggers the FES appropriately when an abnormality is detected in these secondary gait parameters is further described below.

FIG. 13 is a block diagram illustrating the manner in which multiple FES are triggered based on the secondary gait parameters. In block 1310, the gait is computed as described with reference to FIG. 12. The gait is provided to block 1320. In that, the secondary parameters like cadence, stride length, gait speed, balance, and energy consumption are determined with reference to the corresponding object reference in the database 1330. In block 1340, the abnormality in the secondary gait parameter is detected from the standard values of the secondary gait parameter stored in the database 1350. In block 1360, the system determines the set of muscle responsible for the deviation in the secondary muscle. The determination may be made based on the number of iterative and learning stored in the database 1370. In block 1380, the system, triggers the FES attached to the set of muscles determined in block 1360. As a result, plurality of muscles are triggered in sequence or together based on the number of measurements. Due to triggering of FES based on the secondary characteristics and temporal and spatial conditions, walking on a regular surface, walking on a slippery surface, avoiding obstacles in the path etc may be controlled and managed. The manner in which the plurality of the systems described above may be networked to provide better learning and connectivity with external applications is further described below.

FIG. 14 is the environment in which the various aspect of the present disclosure is operative. The environment is shown comprising, FES systems 1401-1403, wireless network 1420, cloud platform 1430, database 1450, and user systems 1460. The FES systems 1401-1403 operate and represent the systems and apparatus described in the sections above. Cloud platform 1430 represents the virtual environment, virtual servers, Software as Service as is well known in the art. The database 1450 represents a centralized database in which the measurements and other data may be stored and accessed by the FES system 1401-1403, cloud platform 1430, and user systems 1460. Wireless network 1420; provide connectivity among the FES system 1401-1403, cloud platform 1430, and user systems 1460. In one embodiment, the FES system measurements, triggering points, current ratings, images, estimates, intent, and reference trajectories of each FES system 1401-1403 are updated in the database 1450 and made available to the user systems 1460 through cloud platform. As a result, the behavior of the muscle over a period time may be remotely monitored and corrected. Further, the gait cycle, intent and trigger points of one FES system 1401 may be adjusted or changed based on the gait cycle, intent and trigger points of the other FES system 1403 (at least when two FES systems are applied for same or similar muscle disorder).

In one embodiment, the FES system 100 (1401-1403) are deployed for gamification as against the conventional gamification systems that allow a patient to interact with a gaming environment with only kinect like sensor and IMU. Integration of FES system for gamification improves rehabilitation. In that, the wearable FES may be strapped onto the desired body part and rotations/motion is mapped onto the game controls. As a result, the playing game initiates the cognitive actions and the FES attached to the body part may be activated appropriately as per the game control. Alternatively, a closed loop control in the game is provided, where the player may be stimulated to help reach a desired objective in the game. Such operation may establish synchronization between the brain and the action and thereby may provide faster remedy or healing of the disorder.

While various embodiments of the present disclosure have been described above, it should be understood that they have been presented by way of example only, and not limitation. Thus, the breadth and scope of the present disclosure should not be limited by any of the above-discussed embodiments, but should be defined only in accordance with the following claims and their equivalents.

What is claimed is:

1. A system for stimulating a muscle comprising:
   a set of stimulators is configured for stimulating a first set of muscles within a first body part;
   a first set of sensors configured for providing a first measurement comprising a set of electromyograms (EMG) from a second set of muscles coupled to the first body part;
   a second set of sensors mounted in a vicinity of the set of stimulators and the first set of sensors, configured for providing a second measurement representing a motion and an orientation of the first body part;
   a third set of sensors consisting at least one of a camera, an infrared sensor, sound sensor, near field sensor, radar sensor configured for providing a third measurement representing a spacial relation between an external object and the first body part;
   a first processor generating a position estimate of the first body part at a first time instance from the first, second, third measurements;
   a second processor adjusting at least one of a time duration, a trigger instance, and a trigger strength of the set of stimulators; and
   a comparator configured for generating a position error as a difference between the position estimate comprising a first position, an orientation and a direction of motion of the first body part and a reference trajectory and the second processor adjusting at least one of the time duration, the trigger instance, and the trigger strength of the set of stimulators to reduce the position error,
   wherein the second set of sensors comprising a set of flex sensors and an inertial measurement unit (IMU) configured to be mounted over the first body part, in that the set of flex sensors is configured for providing flex sensor measurements and the IMU is configured for providing IMU measurements, and the position estimate is determined after correcting the IMU measurements from the flex sensor measurements.

2. The system of claim 1, wherein the third set of sensors comprising a set of cameras configured for mounting over a third body part for providing a sequence of images each comprising the first body part and an object present in the condition that is external to the first body part.

3. The system of claim 2, wherein the first processor is operative to determine the distance between the object and the first body part in the sequence of images and to determine an orientation of the object with respect to the first body part in the sequence of images and the second processor is operative to trigger the set of stimulators with a first trigger strength when the distance is within a first reference range and to trigger the set of stimulators with a second trigger strength that is greater than the first trigger strength when the distance is within a second reference range that is closer to the object.

4. The system of claim 3, wherein the second processor is further configured to triggering the set of stimulators with a third trigger strength when the distance is within the first reference range and the orientation of the object is vertical, and to triggering the set of stimulators with a fourth trigger strength that is greater than the third trigger strength when the distance is within the second reference range and the orientation of the object is vertical.

5. The system of claim 4, further comprising an apparel configured for wearing over the first and a second body part, in that, the set of stimulators and the first set of sensors are embedded such that the set of stimulators configured to stimulate first set of muscle and the first set of sensors is configured to sense the second set of muscles muscle in the first body part when the apparel is worn wherein the apparel further comprises a error indicator that is configured to indicate an error when the first set of sensors in the apparel is not worn appropriately.

6. The system of claim 5, further comprising a memory to store a set of reference positions generated from the first, second and third measurements.

7. The system of claim 6, further comprising a reference position generator configured for generating the set of reference positions of the first body part from the first, second and third measurements and a trajectory generator is configured for generating a set of intermediate positions of the first body part between the set of reference positions.

8. The system of claim 7, wherein the comparator is further configured to generate the position error as a difference between the first position and the corresponding ones of reference position and the intermediate position.

9. The system of claim 8, wherein the set of reference positions comprises a plurality of gait positions of a limb in a gait cycle and the set intermediate positions comprises the plurality of positions of the limb between two successive gait positions.

10. The system of claim 9, wherein the plurality of positions of the limb between two successive gait positions are determined from at least one of a cadence, stride length, gait speed, balance, and energy consumption in the gait cycle.

11. The system of claim 10, further comprising a wireless communication module to transfer and receive an information to and from a central server system and a database, in that, the first, second, third measurements, the position error, the time duration, the trigger instance, and the trigger strength are transferred to the database and the plurality of positions of the limb between two successive gait positions, the cadence, stride length, gait speed, balance, and energy consumption in the gait cycle are received from the database.

* * * * *